(12) United States Patent
Snyder et al.

(10) Patent No.: US 6,249,563 B1
(45) Date of Patent: Jun. 19, 2001

(54) X-RAY DETECTOR ARRAY MAINTAINED IN ISOTHERMAL CONDITION

(75) Inventors: Douglas J. Snyder, Brookfield; Carey S. Rogers; Brian J. Graves, both of Waukesha, all of WI (US)

(73) Assignee: General Electric Company, Waukesha, WI (US)

( * ) Notice: Subject to any disclaimer, the term of this patent is extended or adjusted under 35 U.S.C. 154(b) by 0 days.

(21) Appl. No.: 09/456,629

(22) Filed: Dec. 8, 1999

(51) Int. Cl.$^7$ .................................................. G01N 23/00
(52) U.S. Cl. .................................................. 378/19; 378/4
(58) Field of Search .............................. 378/19, 22, 39, 378/4, 20, 11

(56) References Cited

U.S. PATENT DOCUMENTS

| | | | |
|---|---|---|---|
| 4,283,817 | * | 8/1981 | Cotic ..................................... 29/25.16 |
| 4,709,559 | * | 12/1987 | Dotzauer et al. ....................... 62/499 |
| 5,486,703 | * | 1/1996 | Lovin et al. ....................... 250/492.3 |
| 5,596,228 | * | 1/1997 | Anderton et al. .................... 257/714 |

FOREIGN PATENT DOCUMENTS 0 240 718 A1 * 10/1987 (EP) .

OTHER PUBLICATIONS

"HP–1 Heat Pipe", Product Data Guide, Thermacore, Inc., h–1.p.65, Aug. 7, 1998.

* cited by examiner

Primary Examiner—Robert H. Kim
Assistant Examiner—Irakli Kiknadze
(74) Attorney, Agent, or Firm—Jenkens & Gilchrist

(57) ABSTRACT

X-ray detector apparatus is provided for use in a CT imaging system having a rotatable gantry. The apparatus comprises a selected number of X-ray detector cells and two curved rails, which hold the detector cells in an array comprising an arcuate configuration and mount them onto the gantry for rotation therewith. Conduit segments are distributed along the rails, each conduit segment being proximate to a corresponding group of X-ray detector cells, and a quantity of selected working fluid and a porous wick structure is sealably enclosed in each conduit segment. The fluid is disposed to move along a conduit segment in gaseous form by means of convection, and to move in the opposing direction through the wick structure, in liquid form, by means of capillary action Heat is thereby transferred along a conduit segment to maintain a substantially isothermal condition among the detector cells proximate thereto.

17 Claims, 4 Drawing Sheets

X-RAY DETECTOR ARRAY MAINTAINED IN ISOTHERMAL CONDITION

BACKGROUND OF THE INVENTION

The invention disclosed and claimed herein is generally directed to an array of X-ray detector cells, such as are used in a computed tomography (CT) imaging system, wherein the cells of the array are maintained in a substantially isothermal, or constant temperature, condition. More particularly, the invention pertains to a detector array of the above type which is provided with means for rapidly transferring heat from higher temperature locations to lower temperature locations, in order to acheive the isothermal condition. Even more particularly, the invention pertains to a detector array of the above type wherein the heat transfer means are comparatively simple and inexpensive, and operate with a high degree of efficiency.

In a CT imaging system or scanner, a gantry ring rotates an X-ray tube around a patient or other object of scanning. X-radiation projected by the tube, which is not absorbed by intervening patient body structure, is sensed by respective detectors of a detector array which is also mounted to the gantry ring. In certain classes of CT products, such as those manufactured by the General Electric Company, the assignee herein, the array comprises solid state detectors or detector cells which generate electric signals corresponding to the sensed radiation. The signals are coupled to a data acquisition system, and data acquired thereby is in turn coupled to an image processor which reconstructs an image of patient body structure or other object of interest. In a common arrangement, the detector cells are mounted to the gantry ring or plate by means of two curved rails, which trap or hold respective detector cells between them to form an array having an arcuate configuration.

In the design of a solid state CT detector array, it is essential to maintain respective X-ray detectors of the array at a fixed temperature, in order to maintain a constant gain at the detectors. If the temperature of the detectors changes, their respective electric signal outputs, for a given dose of X-radiation, will also change. In addition, it is very desirable to hold all the detectors at substantially the same temperature (within a few degrees) in order to prevent movement of adjacent wires or other structure, which could partially block some of the detectors from receiving X-rays. Moreover, the detector mounting rails also support a pair of collimator plates for each detector cell. The collimator plates of a given detector cell are selectively spaced apart, to determine the incident X-ray radiation received thereby. If the detector mounting rails experience thermal deflection, i.e., motion or flexure caused by a temperature gradient along the rails, the spacing between some of the collimator plates may change. This, in turn, will effect the amounts of radiation received by the corresponding detectors.

In view of the problems caused by temperature variations, efforts have been made in the past to maintain an X-ray detector array in an isothermal condition, that is, to maintain a substantially constant temperature at all detectors of the array and along the rails thereof. To this end, heating elements have been placed at selected locations with respect to the rails, and heating strips are placed along the rails to distribute heat. However, it has been found that even with these arrangements, holding a uniform temperature on the rails, under all scanning conditions, tends to be very difficult. The rails rely on thermal conduction to move heat from one region to another, since the heating elements do not supply the appropriately distributed heat load for all possible detector operating conditions. Heat transfer in currently used rail designs requires that a temperature gradient be developed, and may proceed too slowly for present operational needs. Moreover, the temperature gradient in the detector mounting rails can change under different scanning configurations. In addition, the rails can be deflected by thermal gradients that are developed in the gantry plate to which the rails are attached. This plate currently is not thermally controlled. The gantry plate has power supplies mounted to it that can produce large thermal gradients, and these gradients may change as the gantry plate rotates during scanning.

SUMMARY OF THE INVENTION

The invention is generally directed to apparatus for detecting X-rays, projected by an X-ray tube or the like, and comprises a selected number of X-ray detector cells and a frame disposed to join the detector cells together to form an array. The frame also orients the detector cells to collectively receive the projected X-rays. The apparatus further comprises a selected number of conduit segments, each conduit segment being joined to the detector array proximate to a corresponding group of X-ray detector cells. A quantity of selected working fluid is sealably contained in respective conduits, and means are positioned within each conduit segment for enabling bidirectional flow of the fluid therein, in order to transfer heat between first and second conduit locations, and to thereby maintain a substantially isothermal condition amongst all the detector cells which are proximate to the conduit segment.

In a preferred embodiment, each conduit segment is provided with an inner wall which encloses an interior space, and the working fluid comprises water. The means for enabling bidirectional flow through each conduit segment comprises a porous material, such as, a material comprising small copper beads or pellets, which are sintered to hold them together. The porous material is attached to the inner wall of a conduit segment, and configured to define a passage through the enclosed space thereof that extends along its length. The porous material is selected in relation to the working fluid so that the fluid, when in liquid form, tends to move through the porous material by means of capillary action. Thus, when a first location along a conduit segment is at a selectively higher temperature than a second location thereof, fluid proximate to the first location is vaporized into gaseous form, and then moves along the conduit passage by means of convection, to the second location. At the second location the fluid is condensed into liquid form, and then flows back toward the first location through the porous material.

Preferably, the frame for the apparatus comprises a rotatable gantry disposed for use with a CT imaging system. Two selectively curved rails, which are fixed in spaced-apart parallel relationship with one another and fixably hold respective detector cells therebetween, mount the detector cells on the gantry, in a selected arcuate configuration, for rotation therewith. In one useful mode, the conduit segments comprise a plurality of linear conduit segments, which are distributed along each of the curved rails. Each of the linear conduit segments is selectively oriented, with respect to the arcuate configuration of detector cells, so that forces generated by acceleration of the rotatable gantry and applied to respective linear segments have directions which are substantially orthogonal thereto. In an alternative mode, only one conduit segment is joined to each of the rails, each conduit being curved to match the curvature of its adjoining rail, and extending along its adjoining rail from one of the ends thereof to the other.

DETAILED DESCRIPTION OF THE PREFERRED EMBODIMENT

Figure 1:
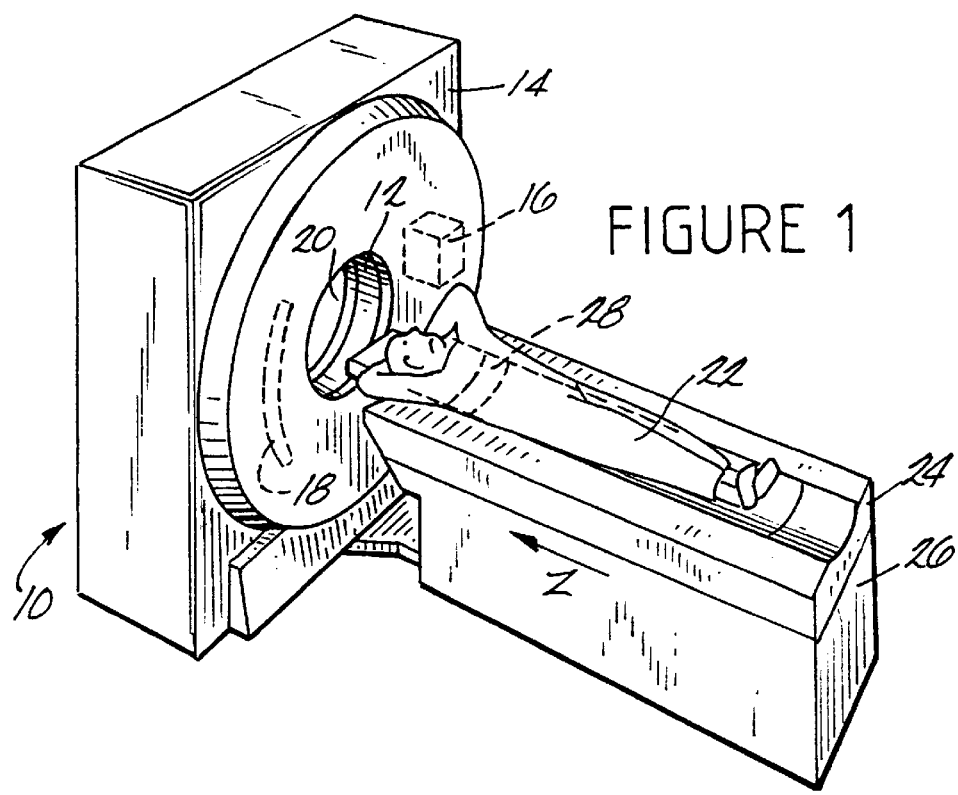
FIG. 1 is a perspective view showing a generalized CT imaging system.

Referring to FIG. 1, there is shown a CT system 10 which includes a gantry frame (shown in FIG. 2) and an annular gantry ring or plate member 12 which is journaled on the frame, or mounted for rotation by means of suitable bearings (not shown). The gantry frame and rotatable gantry plate 12 are contained within a shroud or gantry shielding structure 14.

Referring further to FIG. 1, there is shown an X-ray tube 16 and an X-ray detector array 18 mounted on the rotatable gantry plate 12 for rotation therewith, on opposing sides of a bore 20. A patient 22, positioned on a patient support 24, can be moved along the axis of bore 20 by sliding the support 24 along the direction shown in FIG. 1 by the arrow Z, relative to a base 26. A region or section 28 of the patient 22 may thereby be positioned within the bore 20. Thereupon, gantry plate 12 is driven to rotate tube 16 and detector 18 to acquire CT scan data of the patient section 28, in accordance with conventional practice. The data is then employed to construct an image of the scanned section, likewise in accordance with conventional techniques.

Figure 2:
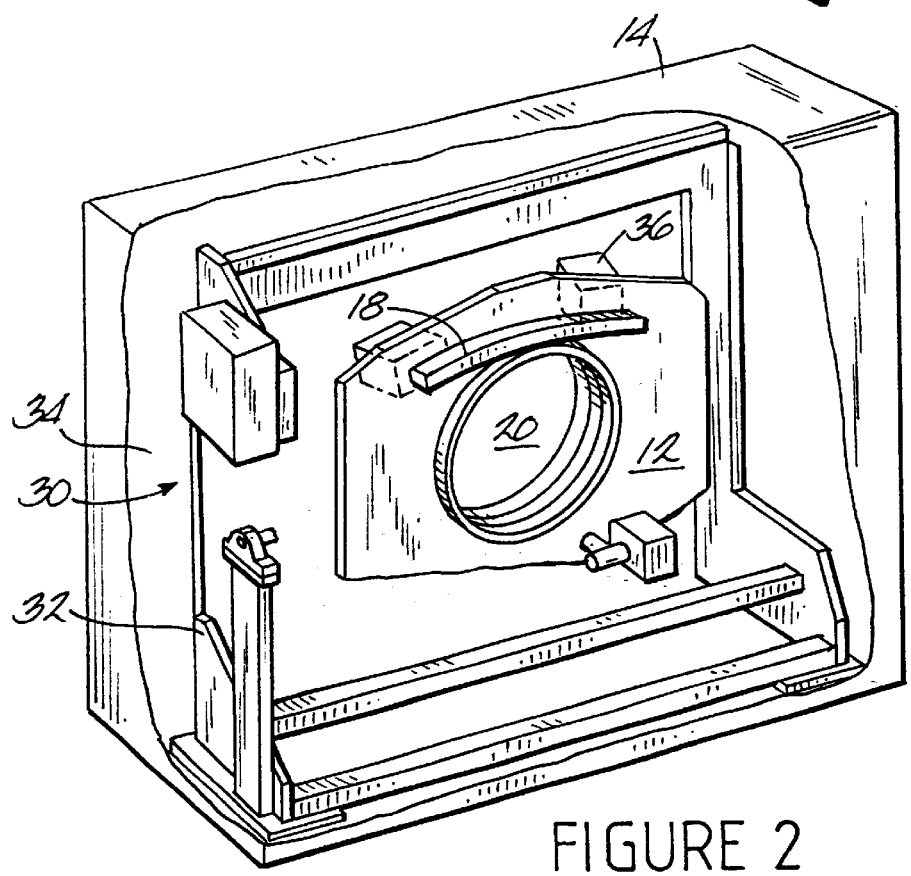
FIG. 2 is a perspective view showing the system of FIG. 1, wherein the gantry shielding has been partly removed to reveal certain system components including the gantry and an X-ray detector array provided with an embodiment of the invention.

Referring to FIG. 2, there is shown gantry 30, including rotatable plate 12 and gantry frame 32, positioned within an enclosure 34 formed by the shielding 14. FIG. 2 further shows a power supply 36 mounted on rotatable gantry plate 12, proximate to detector array 18, for furnishing power to the data acquisition system or other conventional CT electronic components (not shown) which are likewise mounted on rotatable gantry plate 12. Detector 18, comprising an array of solid state detector cells, usefully comprises a product of assignee General Electric Company. As is well known in the art, respective cells of detector 18 produce electric signals representing X-ray radiation respectively received or sensed thereby. The electric cells are processed in accordance with techniques well known in the art, for use by a system image processor (not shown) to construct a desired CT image.

Figure 3:
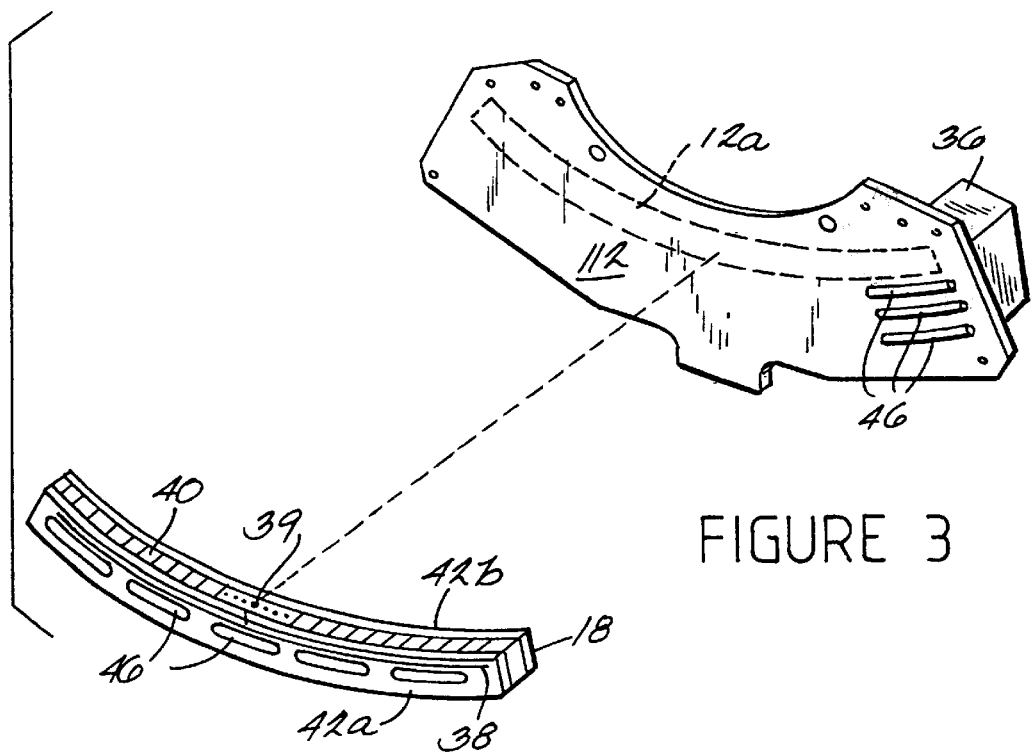
FIG. 3 is an exploded perspective view showing selected components of the embodiment of FIG. 2 in greater detail.

Referring to FIG. 3, there is shown a heater or heating element 38 joined to and extending along a side of detector array 18. A similar heating element (not shown) extends along the opposing side of detector array 18. Thus, heating elements 38, which respectively comprise controllable conventional devices, serve as heat sources which may be operated to provide heat to detector array 18, in an effort to maintain respective detectors of the array at a constant temperature. However, as stated above, prior art arrangements using heaters such as heating elements 38 are frequently unable to effectively distribute heat among the respective detector cells of an array, in order to maintain all the detector cells in an isothermal condition, i.e., within a specified temperature range. More particularly, such arrangements tend to be controlled by a single sensor element 39 located at the midpoint of the detector array. Sensor element 39 operates to turn the heating elements 38 on, when the temperature proximate to the location of sensor 39 drops below a lower temperature limit, and to turn the heating elements off when such temperature rises above an upper temperature limit. The single sensor 39 may thus be able to maintain nearby detector cells at temperatures within a specified narrow range. However, the single sensor will not be very responsive to detector cells at the ends of detector array 18. Accordingly, it will not be effective in maintaining a uniform or even substantially uniform temperature throughout the array. This would require multiple sensors distributed along the detector array, and generally would require a much more complicated arrangement.

Referring further to FIG. 3, there is shown power supply 36 joined to gantry plate 12 proximate to a region 12a, but on the side of gantry plate 12 which is opposite to region 12a. Region 12a comprises the portion of gantry plate 12 which is contacted by detector array 18 when the detector array is joined thereto. Because of its location, power supply 36 functions as an uncontrolled source of heat which tends to affect the end of the detector array which is adjacent thereto much more than the opposing end. Such placement of power supply 36 has been found to have a number of design advantages. However, the heat generated thereby further complicates the task of maintaining respective detectors of array 18 in an isothermal condition.

Figure 4:
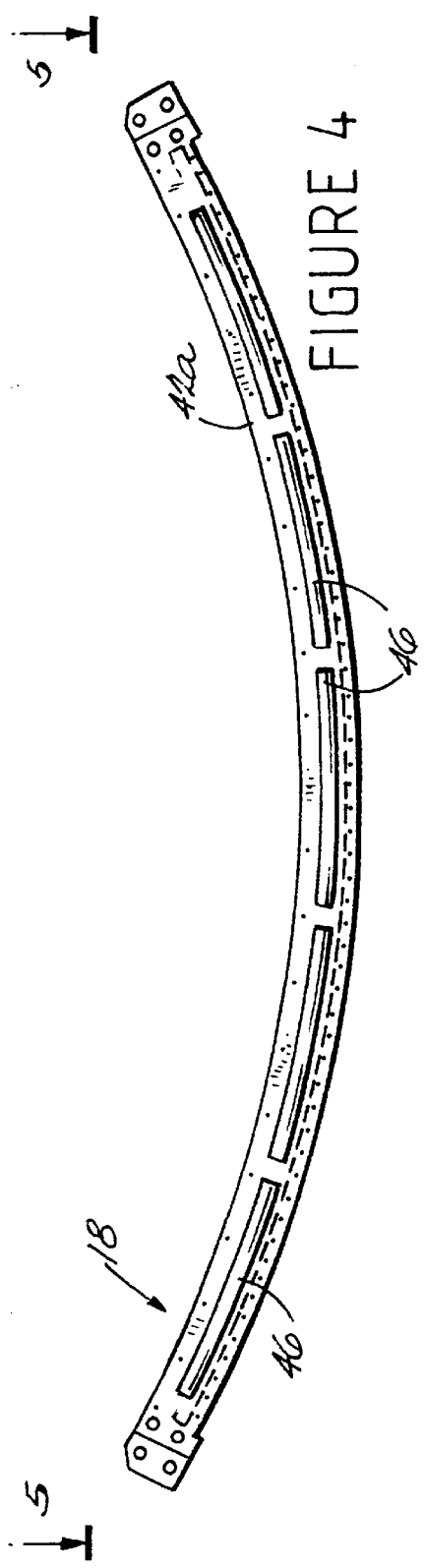
FIG. 4 is a side view showing the detector array of FIG. 2 in greater detail.
Figure 5:
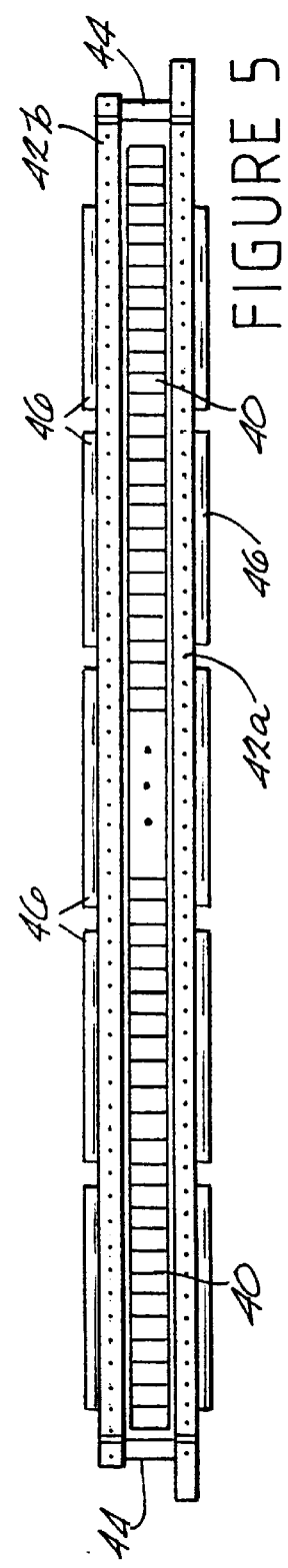
FIG. 5 is an overhead view taken along lines 5—5 of FIG. 4.

Referring to FIGS. 4 and 5 together, there is shown X-ray detector array 18 comprising a pair of selectively curved rails or rail members 42a and 42b, which are fixed in closely-spaced parallel relationship by means of spacers 44 or the like. As best shown by FIG. 5, a large number of X-ray detector cells 40, typically in excess of 100, is held or trapped between rails 42a and 42b, in an arcuate configuration determined by the curvature of the rails.

Usefully, each detector cell 40 comprises a solid state X-ray detector, as is described for example, in commonly assigned U.S. Pat. No. 5,521,387, issued to Riedner et al. In accordance therewith, a solid state detector cell 40 comprises a scintillator body formed of a polycrystalline ceramic scintillator material, such as a product sold by the General Electric Company under the trademark Lumex. When X-radiation is incident upon the scintillator body, the body scintillates at a predetermined wavelength, thereby converting the incident X-radiation into lower energy radiation in the visible or near-visible spectrum, i.e., into light energy. Accordingly, the X-ray detector cell 40 further comprises a device (not shown) for detecting the visible spectrum or scintillator energy which is produced by the scintillator body. The photo diode device is coupled to the scintillator body to produce an electric signal which is proportional to or otherwise represents the intensity of the X-radiation received by the scintillator body.

As stated above, it is essential to maintain each of the detector cells 40 and the rails 42a and 42b in an isothermal condition, that is, at a uniform temperature to within a specified number of degrees. This is necessary to insure that the detectors 40 operate with maximum accuracy, as well as to minimize deflections of the rails supporting the detectors 40, which can be caused by thermal gradients in the rails and in the gantry plate 12 adjacent thereto. Thus, in accordance with the invention, a number of heat transfer devices 46, respectively comprising fluid filled linear conduit segments, are distributed along one or preferably both of the detector support rails 42a and 42b. Each of the heat transfer devices 46 comprises a heat pipe or like device of extremely high conductivity, as described hereinafter in further detail in connection with FIG. 6. FIGS. 4 and 5 show each of the linear heat transfer devices 46 positioned in proximate relationship with a corresponding group of X-ray detector cells 40. Thus, if one location in a group of detectors is at a different temperature than another location therein, the devices 46 proximate to the group will act to rapidly transfer heat from the location of higher temperature to the location of lower temperature, until both locations are at the same temperature. FIGS. 4 and 5 further show the ends of adjacent devices 46 positioned along a rail to be in closely spaced relationship, to enhance heat distribution along the entire length of each rail.

As shown by FIG. 3, the heat transfer devices 46 are mounted on the rails 42a and 42b proximate to the heating elements 38. Thus, heat may readily be transferred from a hotter region of the detector rails to a cooler region even in the almost complete absence of a thermal gradient. Moreover, the heating elements 38 in this arrangement do not require any more sensors than the single sensor 39. The heat transfer devices 46 are passive, acoustically silent, have extremely high reliability, and are relatively inexpensive.

Referring further to FIG. 3, there is shown a configuration comprising several more heat transfer devices 46 which are mounted upon gantry plate 12, very close to power supply 36. These additional devices 46 act to reduce thermal gradients in gantry plate 12, in the region thereof at which rails 42a and 42b are attached, and thereby act to reduce deflections therein. As a further benefit, the additional heat transfer devices reduce temperatures in power supply 36, leading to improved reliability of electronics associated therewith.

Figure 6:
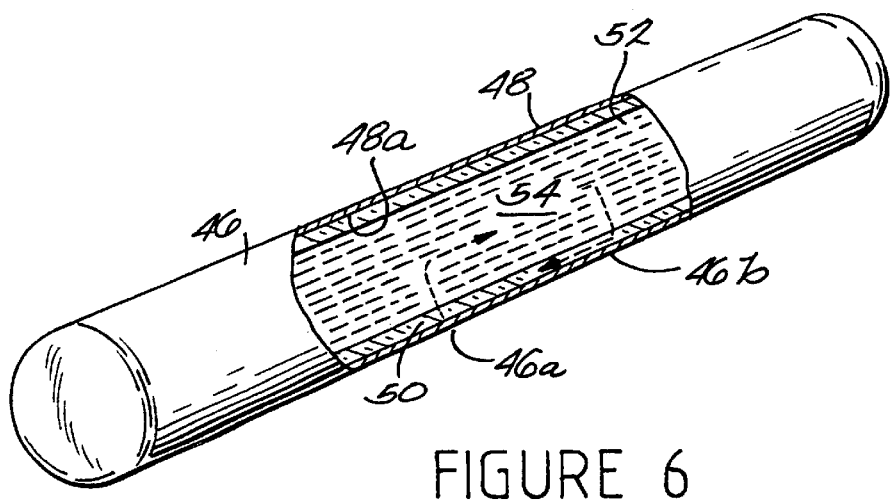
FIG. 6 is a perspective view of a heat transfer device, with a section broken away, for the embodiment of FIG. 2.

Referring to FIG. 6, there is shown a linear heat transfer device 46 comprising a length of copper tubing or conduit 48, which is tightly closed or sealed at its ends to form a vacuum tight vessel. The vessel is evacuated and partially filled with a working fluid 52, such as water. Heat transfer device 46 is usefully of circular cross section. FIG. 6 further shows a porous metal wicking structure 50, which is joined to the inner wall or surface 48a of copper conduit 48. Porous wicking structure 50 is usefully formed of a material such as the material formed of copper pellets, as described above, and is configured to surround or define a passage 54 which extends along the length of transfer device 46.

By providing heat transfer device 46 with the construction shown in FIG. 6, such device is enabled to transfer heat by respective evaporation and condensation of working fluid 52. More particularly, if point 46a along device 46 is at a higher temperature than a location 46b spaced apart therefrom, heat is inputted through conduit 48 into the interior thereof, proximate to location 46a. As a result, fluid 52 is vaporized in passage 54 proximate to location 46a. This creates a pressure gradient in passage 54, between a region proximate to location 46a and a cooler region proximate to location 46b. This pressure gradient forces the vaporized fluid to flow along passage 54 to the cooler region, where it condenses into a liquid and gives up its latent heat of vaporization. The working fluid 52, now in liquid form, then flows in the opposite direction along device 46, back toward location 46a, through the porous wick structure 50.

Such fluid motion is caused by capillary action in the wick structure 50, or by gravity if device 46 is oriented to decline downwardly from location 46b to location 46a. Usefully, each of the heat transfer devices 46 comprises a device which is similar to a product sold by Thermacore Inc. and referred to commercially thereby as a heat pipe. Devices of such type may have an effective thermal conductivity which exceeds the thermal conductivity of copper by more than $10^3$ times.

Figure 7:
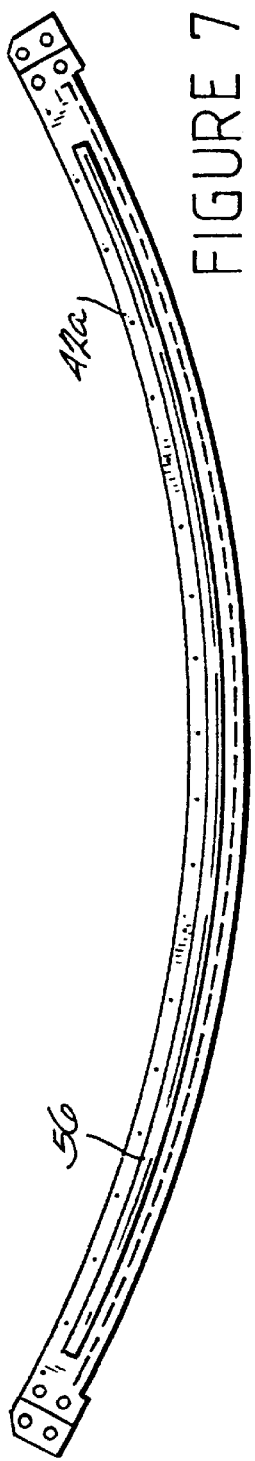
FIG. 7 shows a modification of the invention.

Referring to FIG. 7, there is shown a modification of the invention, wherein a single heat transfer device 56 is joined to each rail 42a and 42b, rather than a number of linear devices 46 as described above. While each heat transfer device 56 has the same internal construction as a device 46, it is curved to match the curvature of its adjoining rail, and extends along its adjoining rail in close proximity to each of the detector cells 40 supported thereby.

It has been recognized that when the gantry rotates, an acceleration load is developed, which may be applied to the heat transfer devices. It could be very undesirable if a significant component of the acceleration load was directed along the axis of a linear heat transfer device 46.

Figure 8:
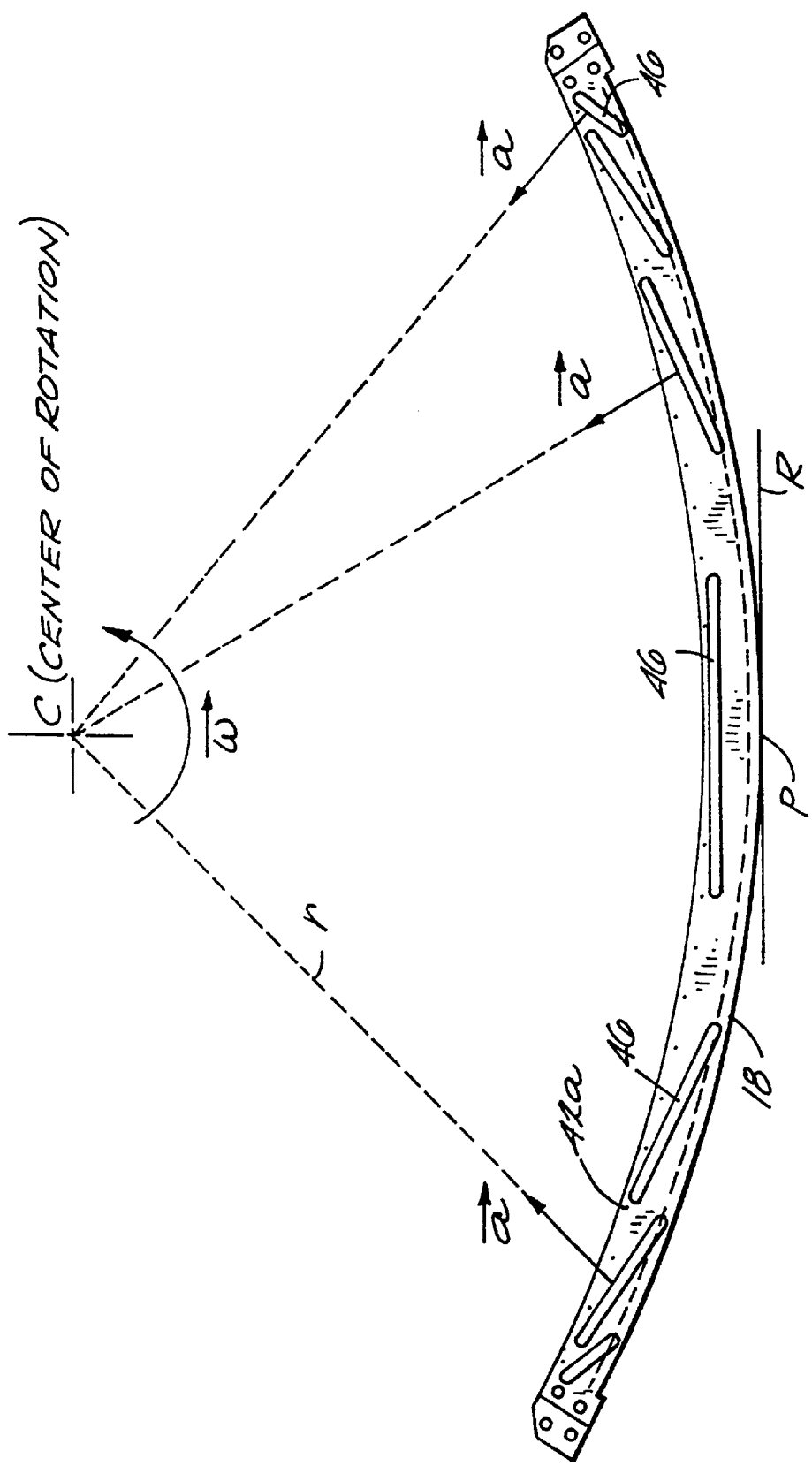
FIG. 8 shows a further modification of the invention

This acceleration load or force could impede the capillary movement of fluid 52 through porous material 50, and thereby interfere with the heat transfer process. Accordingly, FIG. 8 shows a second modification of the invention. In FIG. 8, a number of linear heat transfer devices 46 are distributed along detector support rail 42a, as described above in connection with FIGS. 4 and 5. However, instead of following the curvature of the rail, each of the linear devices 46 is oriented at a selected angle with respect to an axis R, which may be selected to be a line which is tangent to the outer diameter of rail 42a at the mid-point P thereof. More particularly, each of the linear heat transfer devices 46 is oriented so that forces generated by acceleration of the rotatable gantry plate 12 and applied to respective linear devices 46 have directions which are substantially orthogonal thereto, as depicted by arrows a in FIG. 8. It will be appreciated that devices 46 would also be similarly attached along rail 42b. In FIG. 8, the vector co is the angular velocity of gantry plate 12 and detector 18.

Usefully, if detector array 18 is rotated by gantry plate 12 around a circular path having a center at point C, each of the devices 46 is oriented so that a line r, extending from point C to the midpoint of a device, is at an angle of 90° with the axis thereof. An acceleration force directed through the midpoint of the device will thus be orthogonal thereto, and will not effect fluid flow along the device by capillary action. If an acceleration force is not perfectly orthogonal to the device, the effect on fluid flow will still be negligible, if the device is sufficiently short. However, the greater the departure from being orthogonal, the greater the degradation of capillary action will be, and the shorter the heat pipe will need to be. Generally, in the arrangement of FIG. 8, using a larger number of devices 46, each of reduced length, will diminish the adverse effects of acceleration forces applied thereto. However, as the number of devices 46 is increased, the number of spaces between adjacent heat transfer devices also increases, which tends to inhibit heat transfer along detector array 18. It is anticipated that one of skill in the art will be able to determine the proper balance between these two considerations for a particular application.

Obviously, many other modifications and variations of the present invention are possible in light of the above teachings. It is therefore to be understood that within the scope of the disclosed concept, the invention may be practiced otherwise than as has been specifically described.

What is claimed is:

1. Apparatus for detecting X-rays projected by an X-ray source comprising:

a selected number of X-ray detector cells;

a frame disposed to join said detector cells together to form an X-ray detector array, and to orient said detector cells to collectively receive said projected X-rays;

a selected number of conduit segments, each of said conduit segments being joined to said detector array proximate to a corresponding group of said X-ray detector cells;

a quantity of selected working fluid sealably contained in each of said conduit segments; and means positioned within a given one of said conduit segments for enabling bidirectional flow of the fluid contained therein, in order to transfer heat along said given conduit segment from a first location to a second location, and to thereby maintain a substantially isothermal condition among respective detector cells of the detector cell group which is proximate to said given conduit segment.

2. The apparatus of claim 1 wherein:

said given conduit segment is provided with an inner wall which encloses an interior space; and said means for enabling said bidirectional flow comprises a porous material attached to said inner wall and configured to define a passage through said enclosed space that extends along the length of said given conduit segment, said porous material being selected in relation to said working fluid so that said fluid, when in liquid form, is disposed for movement through said porous material by means of capillary action.

3. The apparatus of claim 2 wherein:

when said first location is at a selectively higher temperature than said second location, fluid proximate to said first location is vaporized into gaseous form, moved along said passage by means of convection to said second location, and then condensed into liquid form.

4. The apparatus of claim 3 wherein said frame comprises:

a rotatable gantry plate disposed for use with a CT imaging system; and rail structure for mounting said X-ray detector cells on said gantry in a selected arcuate configuration, for rotation therewith.

5. The apparatus of claim 4 wherein:

said conduit segments comprise a plurality of linear conduit segments respectively distributed along said rail structure, each of said linear conduit segments being selectively oriented, with respect to said gantry plate, so that forces generated by acceleration of said rotatable gantry plate and applied to respective linear conduit segments have directions which are substantially orthogonal thereto.

6. The apparatus of claim 5 wherein:

said rail structure comprises two selectively curved rails, which are fixed in spaced-apart parallel relationship and fixably hold said detector cells therebetween; and a plurality of said linear conduit segments are distributed along each of said curved rails.

7. The apparatus of claim 4 wherein:

said rail structure comprises two selectively curved rails, which are fixed in spaced-apart parallel relationship and fixably hold said detector cells therebetween; and a single one of said conduit segments is joined to each of said rails, each of said conduit segments being curved to match the curvature of its adjoining rail and extending along its adjoining rail from one of the ends thereof to the other.

8. The apparatus of claim 4 wherein:

each of said detector cells comprises a solid state detector cell disposed to produce a signal representing the amount of X-radiation which is received thereby.

9. The apparatus of claim 4 wherein:

an electronic component disposed to generate heat is mounted on said gantry plate in selected relationship with said rail structure, and an additional number of said conduit segments, each containing a quantity of said working fluid, are joined to said gantry plate proximate to said electronic component.

10. The apparatus of claim 6 wherein:

each of said rails is rotated around a specified center of rotation; and some of said conduit segments are distributed along each of said rails, each of the conduit segments distributed along a given rail being oriented with respect thereto so that a line extending between said center of rotation and the midpoint of a particular conduit segment thereon is substantially orthogonal to the axis of the particular conduit segment.

11. Apparatus for detecting X-rays projected by an X-ray source comprising:

a detector array comprising a number of X-ray detector cells disposed to receive said X-rays, and further comprising a pair of rails joining said detector cells in fixed relationship with one another;

a plurality of conduit segments selectively distributed along at least one of said rails, each of said conduit segments provided with an inner wall;

a porous material positioned around the inner wall of each of said conduit segments and surrounding a passage which extends along the length thereof; and a quantity of selected working fluid sealably contained in each of said conduit segments, the working fluid in a given conduit segment, when the temperature at a first position of said given conduit segment is selectively higher than the temperature at a second position thereof, being disposed to flow in gaseous form from said first position to said second position through said passage, and to flow in liquid form from said second position to said first position through said porous material, said fluid flow resulting in the transfer of heat along a portion of one of said rails which is adjacent to said given conduit segment.

12. The apparatus of claim 11 wherein:

each of said rails is rotated around a specified center of rotation; and the conduit segments distributed along a given one of said rails are selectively oriented, with respect to said given rail, so that forces generated by acceleration of said detector array and applied to respective linear conduit segments of said given rail have directions which are substantially orthogonal thereto.

13. The apparatus of claim 12 wherein:

each of said conduit segments distributed along said given rail is oriented with respect thereto so that a line extending from said center of rotation to the midpoint of a particular conduit segment thereon is orthogonal to the particular conduit segment.

14. The apparatus of claim 13 wherein:

said detector array is mounted upon a rotatable gantry plate disposed for use in a CT imaging system.

15. The apparatus of claim 14 wherein:

an electronic component disposed to generate heat is mounted on said gantry plate in selected relationship with said detector array, and an additional number of said conduit segments, each containing a quantity of said working fluid, are joined to said gantry plate proximate to said electronic component to distribute said generated heat, and to thereby maintain said gantry plate in a substantially isothermal condition.

16. Apparatus for detecting X-rays projected by an X-ray source comprising:

a detector array comprising a number of X-ray detector cells disposed to receive said X-rays, and further comprising a pair of rails joining said detector cells in fixed relationship with one another;

a conduit segment extending along most of the length of a selected one of said rails, said conduit segment provided with an inner wall;

a porous material positioned around the inner wall of said conduit segment and surrounding a passage which extends along the length thereof; and a quantity of selected working fluid sealably contained in said conduit segment, said working fluid, when the temperature at a first position of said conduit segment is selectively higher than the temperature at a second position thereof, being disposed to flow in gaseous form from said first position to said second position through said passage, and to flow in liquid form from said second position to said first position through said porous material, said fluid flow resulting in the transfer of heat along the portion of said selected rail which is adjacent to said conduit segment.

17. The apparatus of claim 16 wherein:

said selected rail and said conduit segment are respectively curved to lie along the arc of a circle.

* * * * *